United States Patent
Mikula et al.

(10) Patent No.: US 12,390,368 B2
(45) Date of Patent: Aug. 19, 2025

(54) NONLINEAR OPTICAL DEVICE FOR MICRO-MACHINING OF THE CORNEAL EPITHELIUM

(71) Applicant: The Regents of the University of California, Oakland, CA (US)

(72) Inventors: Eric Mikula, Rancho Santa Margarita, CA (US); James V. Jester, Irvine, CA (US); Tibor Juhasz, Corona del Mar, CA (US); Samantha Bradford, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 762 days.

(21) Appl. No.: 17/603,830

(22) PCT Filed: Apr. 24, 2020

(86) PCT No.: PCT/US2020/029893
§ 371 (c)(1),
(2) Date: Oct. 14, 2021

(87) PCT Pub. No.: WO2020/219931
PCT Pub. Date: Oct. 29, 2020

(65) Prior Publication Data
US 2022/0211543 A1 Jul. 7, 2022

Related U.S. Application Data

(60) Provisional application No. 62/839,092, filed on Apr. 26, 2019.

(51) Int. Cl.
*A61F 9/008* (2006.01)
*A61F 9/00* (2006.01)
(Continued)

(52) U.S. Cl.
CPC .......... *A61F 9/0084* (2013.01); *A61F 9/0008* (2013.01); *A61B 2017/0019* (2013.01);
(Continued)

(58) Field of Classification Search
CPC .. A61F 9/008; A61F 9/00802; A61F 9/00825; A61F 9/0084; A61F 2009/00872;
(Continued)

(56) References Cited

U.S. PATENT DOCUMENTS 6,299,307 B1   10/2001   Oltean et al.
6,881,212 B1   4/2005    Clement et al.
(Continued)

FOREIGN PATENT DOCUMENTS

EP   2990016 A1   3/2016

OTHER PUBLICATIONS

PCT International Search Report dated Aug. 6, 2020 in related PCT Application No. PCT/US2020/029893.
(Continued)

*Primary Examiner* — Ahmed M Farah
(74) *Attorney, Agent, or Firm* — Robert D. Buyan; Stout, Uxa & Buyan, LLP

(57) ABSTRACT

A system for creating micro-channels through superficial corneal epithelium, the system including: a femtosecond laser having a pulse energy range of 1 to 20 microjoules (μJ) and a capability of generating a laser beam having a wavelength of 700-1100 nanometers (nm) and a repetition rate of 1 kilohertz to 1 megahertz, a laser delivery system comprising a beam expander, a scanning lens having a numerical aperture (NA) of 0.05 to 0.5 and a focusing objective, and control software that controls the delivery system such that the laser beam is scanned in a pattern. The system is used to noninvasively increase corneal epithelial permeability to therapeutic agents through micron-scale channels created
(Continued)

through the corneal epithelium by the system or to induce wound healing in a cornea in a subject following creation of micron-scale channels in the cornea.

22 Claims, 7 Drawing Sheets

(51) Int. Cl.
  *A61B 17/00* (2006.01)
  *A61B 17/32* (2006.01)
  *A61B 18/00* (2006.01)
  *A61B 18/20* (2006.01)

(52) U.S. Cl.
  CPC .............. *A61B 2017/00194* (2013.01); *A61B 2017/320056* (2013.01); *A61B 2018/00702* (2013.01); *A61B 2018/00761* (2013.01); *A61B 2018/20359* (2017.05); *A61F 2009/00872* (2013.01); *A61F 2009/00897* (2013.01)

(58) Field of Classification Search
  CPC ... A61F 2009/00897; A61B 2018/0057; A61B 2018/00696; A61B 2018/00702; A61B 2018/00732; A61B 2018/00738; A61B 2018/20351; A61B 2018/20353; A61B 2018/20355; A61B 2018/20359; A61B 2017/00181; A61B 2017/0019; A61B 2017/00194; A61N 5/062; A61N 2005/0626; A61N 2005/0659; A61N 2005/0662; A61N 5/067

USPC .................. 606/3, 4, 11, 17, 18; 607/88, 89
  See application file for complete search history.

(56) References Cited

U.S. PATENT DOCUMENTS

| | | | |
|---|---|---|---|
| 2004/0089804 A1 | 5/2004 | Dantus et al. | |
| 2008/0051772 A1* | 2/2008 | Suckewer | A61B 18/20 606/5 |
| 2008/0170218 A1 | 7/2008 | Dantus et al. | |
| 2010/0016783 A1 | 1/2010 | Bourke et al. | |
| 2011/0118713 A1 | 5/2011 | Raksi | |
| 2012/0289886 A1* | 11/2012 | Muller | A61F 9/00804 604/20 |
| 2012/0330291 A1 | 12/2012 | Jester et al. | |
| 2013/0245616 A1 | 9/2013 | Alfano et al. | |
| 2013/0310728 A1 | 11/2013 | Seiler et al. | |
| 2014/0094711 A1* | 4/2014 | Sondermann | A61F 9/00804 606/4 |
| 2015/0290030 A1 | 10/2015 | Suckewer et al. | |
| 2015/0320599 A1 | 11/2015 | Jester et al. | |
| 2016/0151202 A1* | 6/2016 | Scarcelli | A61F 9/008 606/5 |
| 2016/0184135 A1 | 6/2016 | Koenig et al. | |
| 2017/0100282 A1 | 4/2017 | Seiler et al. | |
| 2021/0000646 A1* | 1/2021 | Adler | A61F 9/0079 |

OTHER PUBLICATIONS

Extended European Search Report dated Dec. 2, 2022 in related European Application No. 20794897.7.

* cited by examiner

NONLINEAR OPTICAL DEVICE FOR MICRO-MACHINING OF THE CORNEAL EPITHELIUM

RELATED APPLICATIONS

This application is a 35 U.S.C. § 371 National Stage of PCT International Application No. PCT/US2020/029893 entitled NONLINEAR OPTICAL DEVICE FOR MICRO-MACHINING OF THE CORNEAL EPITHELIUM filed Apr. 24, 2020, which claims priority to U.S. Provisional Patent Application No. 62/839,092 entitled NONLINEAR OPTICAL DEVICE FOR MICRO-MACHINING OF THE CORNEAL EPITHELIUM filed Apr. 26, 2019, the entire disclosure of each such application being expressly incorporated herein by reference.

STATEMENT REGARDING FEDERALLY SPONSORED R&D

This invention was made with government support under EY024600-06, awarded by The National Eye Institute of the National Institutes of Health. The government has certain rights in the invention.

BACKGROUND OF THE INVENTION

Field of the Invention

A femtosecond laser delivery device for the creation of micro-channels through the superficial corneal epithelium to increase delivery of therapeutic agents into the corneal stroma, while maintaining integrity of Bowman's layer, the stroma, and the epithelium surrounding the micro-channels.

Description of the Related Art

The superficial corneal epithelium presents a major barrier to fluorophore/drug delivery into the corneal stroma. Tight junctions in the squamous cell layer of the superficial epithelium are responsible for the relative impermeability of this layer. During certain corneal procedures, such as UVA mediated corneal collagen crosslinking, it is necessary to achieve a certain concentration of riboflavin 5' phosphate in the corneal stroma for sufficient photoactivation of the fluorophore, free oxygen radical generation, and collagen crosslinking. However, the corneal epithelium is impermeable to riboflavin. Thus the gold standard for corneal collagen crosslinking, the so-called Dresden protocol, requires the manual scraping and removal of the corneal epithelium to circumvent the problem of corneal impermeability to riboflavin 5' phosphate. The result is a painful and invasive procedure with increased healing time.

Current solutions to corneal impermeability include (a) corneal epithelial removal: The epithelium is removed altogether and riboflavin is imbibed directly into the stroma; (b) benzalkonium chloride (BAK): This method involves inclusion of the surfactant, BAK, in the riboflavin solution. BAK is a preservative that is toxic to the corneal epithelium and physically disrupts the surface corneal epithelial barrier; (c) sodium ethylenediaminetetraacetic acid (EDTA): This method involves inclusion of the drug EDTA in the riboflavin solution. EDTA chelates divalent cations leading to disassembly of tight junctions and increased corneal epithelial permeability; (d) Ricrolin TE (Horus Pharma): This method involves use of a proprietary riboflavin solution including drugs intended to increase corneal permeability; (e) iontophoresis: This method uses a mild electric field to drive riboflavin through the epithelium and into the stroma across an electric potential gradient; (f) Femtosecond stromal pockets: A femtosecond laser is used to create an intrastromal pocket within the corneal stroma. This pocket is then infused with riboflavin solution before stromal crosslinking takes place.

Near-infrared femtosecond lasers have been used extensively in the corneal stroma to create laser induced optical breakdown (LIOB). LIOB in the stroma has been primarily used for the creation of corneal flaps in LASIK surgery. Anterior stromal puncture is an ophthalmic procedure used to treat bullous keratopathy whereby a 20 gauge needle is used to puncture through the epithelium and Bowman's layer in multiple locations. The purpose is to promote or restore epithelial attachment to Bowman's layer.

SUMMARY OF THE INVENTION

Some embodiments relate to a system for creating microchannels through superficial corneal epithelium, the system including:
  a femtosecond laser having a pulse energy range of 1 to 20 microjoules (μJ) and a capability of generating a laser beam having a wavelength of 700-1100 nanometers (nm) and a repetition rate of 1 kilohertz to 1 megahertz,
  a laser delivery system comprising a beam expander, a scanning lens having a numerical aperture (NA) of 0.05 to 0.5 and a focusing objective, and
  control software that controls the delivery system such that the laser beam is scanned in a pattern.

In some embodiments, the femtosecond laser is a regeneratively amplified femtosecond laser having a pulse duration of 10-500 fs.

In some embodiments, the laser delivery system includes galvo controlled mirrors for control of the laser beam in x, y and z dimensions.

In some embodiments, there are one or more galvo mirrors for control of the laser beam in the x-axis, and one or more galvo mirrors for control of the laser beam in the y-axis.

In some embodiments, there are two galvo mirrors for control of the laser beam in the x-axis, and one galvo mirror for control of the laser beam in the y-axis.

In some embodiments, the scanning lens has a numerical aperture of 0.1-0.3.

In some embodiments, the control software is configured to control delivery of the laser beam in a raster pattern.

Some embodiments relate to a method of noninvasively increasing corneal epithelial permeability to a therapeutic agent, the method including:
  providing a system as disclosed herein;
  using the system to direct the femtosecond laser through the corneal epithelium to create micron-scale channels through the corneal epithelium and no further than the basal epithelial layer, and
  applying the therapeutic agent to the permeabilized corneal epithelium so that the therapeutic agent passes through the micron-scale channels and into the corneal stroma.

In some embodiments, the micron-scale channels are 1-10 μm in diameter and 5-100 μm in axial length.

In some embodiments, the micro-channels are created in a raster pattern.

In some embodiments, the grid pattern has an inter-spot spacing from 25 to 250 μm.

In some embodiments, the therapeutic agent includes a drug and/or a photodynamic agent.

In some embodiments, the drug is riboflavin 5' phosphate.

In some embodiments, a concentration of the riboflavin 5' phosphate delivered to the corneal stroma is about 300 µg/ml.

In some embodiments, the femtosecond laser is used at a 10 µJ pulse energy and a wavelength of about 1030 nm.

In some embodiments, a 6 mm diameter area is treated and the micron-scale channels have a 25-250 µm channel spacing.

In some embodiments, the method enhances the application of non-linear optical photodynamic therapy to the cornea, including directing pulsed infrared laser light at a focal spot at a depth in the cornea, wherein the pulsed infrared laser light within the cornea provides an intensity and a length of irradiation sufficient to cause collagen crosslinking (CXL) effective for corneal stiffening.

In some embodiments, the method enhances the application of non-linear optical photodynamic therapy to the cornea, including directing pulsed infrared laser light at a focal spot at a depth in the cornea, wherein the pulsed infrared laser light within the cornea provides an intensity and a length of irradiation to effectively provide antimicrobial mediation to treat a corneal infection.

In some embodiments, the method enhances the application of non-linear optical photodynamic therapy to the cornea, including directing pulsed infrared laser light at a focal spot at a depth in the cornea, wherein the pulsed infrared laser light within the cornea provides an intensity and a length of irradiation to effectively kill cells, bacteria, tumors or neovascular vessels growing into the cornea.

Some embodiments relate to a method of inducing wound healing in a cornea in a subject including:
  providing a system as disclosed herein; and
  using the system to direct the femtosecond laser through the cornea epithelium and into the stroma of the cornea to create micron-scale channels through the corneal epithelium and into the cornea,
  wherein the micron-scale channels induce wound healing in the cornea.

In some embodiments, the wound healing is accompanied by tacking down of the corneal epithelium to the cornea.

In some embodiments, the subject is treated for an epithelial dystrophy.

DETAILED DESCRIPTION OF THE PREFERRED EMBODIMENT

The following detailed description and the accompanying drawings to which it refers are intended to describe some, but not necessarily all, examples or embodiments of the present disclosure. The described embodiments are to be considered in all respects only as illustrative and not restrictive.

We disclose a device (femtosecond laser, laser delivery system, and control software) capable of carrying out the process of precisely creating micro-channels through the superficial epithelium in a specific, predetermined pattern, while preserving the underlying tissue structures (Bowman's layer, corneal stroma) and epithelium surrounding the channels.

The device and related methods are used to increase the permeability of the corneal epithelium to riboflavin (and other drugs and photodynamic chemical agents) by creating direct access for the molecule through the corneal epithelium and into the corneal stroma via femtosecond laser created micro-channels. Use of the device and methods can non-invasively enable therapeutic levels of riboflavin or other therapeutic agents in the corneal stroma without requiring the removal of the corneal epithelium or causing significant discomfort/damage to the corneal epithelium.

Figure 1:
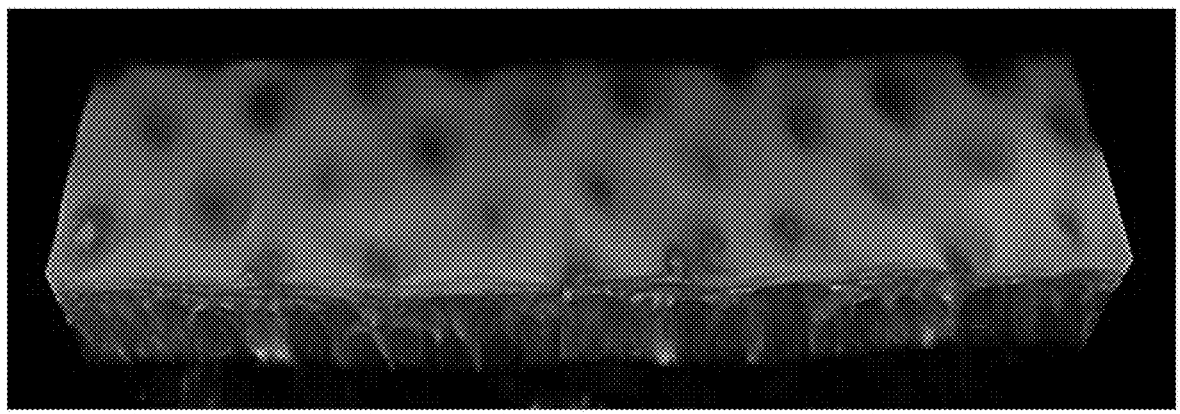
FIG. 1. 3D reconstruction of the surface corneal epithelium of a rabbit cornea treated with non-linear optical micromachining to form channels that are spaced 25 µm apart.

The process comprises using a femtosecond laser and delivery system to non-invasively create micron scale, single laser pulse channels through the corneal epithelium, while preserving Bowman's layer, the corneal stroma, and the epithelium surrounding the channels. In some embodiments, the channels are 1-10 µm in diameter, including diameters of 1 µm, 2 µm, 3 µm, 4 µm, 5 µm, 6 µm, 7 µm, 8 µm, 9 µm and 10 µm. In some embodiments, the axial lengths of the channels are 5 to 100 µm, including 5 µm, 10 µm, 20 µm, 30 µm, 40 µm, 50 µm, 60 µm, 70 µm, 80 µm, 90 µm, and are arranged in a grid pattern with an inter-spot spacing ranging from 25 to 250 µm. Each channel begins at the surface of the epithelium and extends to precise depths which can be controlled to go no further than the basal epithelial layer or into the basal epithelial layer and deeper into the stroma depending on the specific application. A 3D rendering of a grid of micro-channels through the epithelium of a rabbit cornea is presented in FIG. 1. These channels were created in an ex-vivo rabbit eye with our device. Using an axial length of 25 µm creates a channel that preservers Bowman's layer and the anterior stroma, which is advantageous, as disrupting either of these tissues can result in a wound healing response. This wound healing response may or may not be advantageous in certain diseases. A femtosecond laser is necessary as the ultrashort pulse duration minimizes collateral damage to surrounding tissue while enabling precise control and localization of the treated volume to the superficial epithelium. This precision is not guaranteed using mechanical methods such as micro-needling or long pulse duration lasers.

The device comprises a femtosecond laser, a laser delivery system including beam scanning and focusing optics, and control software. The femtosecond laser has a pulse energy range of 1 to 20 microjoules (μJ), a wavelength of 700-1100 nanometers (nm), and a repetition rate of 1 kilohertz (kHz) to 1 megahertz (MHz).

In some embodiments, the femtosecond laser is used with a pulse energy of 1 μJ, 2 μJ, 3 μJ, 4 μJ, 5 μJ, 6 μJ, 7 μJ, 8 μJ, 9 μJ, 10 μJ, 11 μJ, 12 μJ, 13 μJ, 14 μJ, 15 μJ, 16 μJ, 17 μJ, 18 μJ, 19 μJ, 20 μJ or a range defined by any two of the preceding values.

In some embodiments, the femtosecond is used with a wavelength of 700 nm, 750 nm, 800 nm, 850 nm, 900 nm, 950 nm, 1000 nm, 1050 nm, 1100 nm, or a range defined by any two of the preceding values.

In some embodiments, the femtosecond is used with a repetition rate of 1 kHz, 50 kHz, 100 kHz, 150 kHz, 200 kHz, 250 kHz, 300 kHz, 350 kHz, 400 kHz, 450 kHz, 500 kHz, 550 kHz, 600 kHz, 650 kHz, 700 kHz, 750 kHz, 800 kHz, 850 kHz, 900 kHz, 950 kHz, 1 MHz or a range defined by any two of the preceding values.

In general, the device and methods allow more efficient riboflavin and/or drug delivery into the corneal stroma with less side effects, healing time, and patient discomfort than any of the following available alternatives Dresden Protocol: Our procedure is safer and has less side effects compared to the gold standard Dresden protocol as the Dresden protocol involves removal of the epithelium. This should not be considered a reasonable solution to the problem, but rather a circumvention of the problem altogether. The Dresden protocol is saddled with a variety of limitations, the most important being patient discomfort and wound healing response. There is significant corneal haze associated with manual scraping of the epithelium. The standard Dresden protocol results in stromal concentrations of 25-50 ug/mL, roughly 5 times less than we achieved with Nonlinear Micro-Machining of the Corneal Epithelium with the epithelium intact (288 ug/mL) (Mastropasqua, Am J Ophthalmol 2014; 157: 623-630; Lombardo, J Cat Ref Surg 2017; 43: 680-686; Rubinfeld, J Cat Ref Surg 2018; 44:237-242); and our own unpublished measurements).

Benzalkonium chloride (BAK): Our procedure delivers 17 times more riboflavin into the stroma than BAK (our unpublished measurements).

Sodium ethylenediaminetetraacetic acid (EDTA): Our procedure delivers 30 times more riboflavin into the stroma than EDTA (Rubinfeld, J Cat Ref Surg 2018; 44: 237-242; our unpublished results).

Ricrolin TE (Horns Pharma): Our procedure delivers 40 times more riboflavin into the cornea than this commercially available solution. (Mastropasqua, Am J Ophthalmol 2014; 157: 623-630, our unpublished results).

Iontophoresis: Our procedure delivers 19 times more riboflavin into the cornea than iontophoresis.

Femtosecond stromal pockets: Data regarding riboflavin concentration of instrastromal pocket imbibition is not available in the literature. Kanellopoulos (J Ref Surg 2009; 25: 1034-1037) showed a halt in the progression of KC at 3 months using this technique. Seiler et al (IOVS 2014; 55: 4261-4265) showed similar changes in mechanical strength of corneas crosslinking using Dresden protocol and intrastromal pocket riboflavin imbibition. This method has not attained traction in the clinic. Importantly, creating an intrastromal pocket is disruptive to the corneal collagen architecture. Thus, disrupting a significant portion of cornea architecture in the name of increased drug delivery is not well justified for a procedure seeking strengthen corneal biomechanical properties.

Overall, our procedure delivers at least 20 times more riboflavin into the stroma than any other epithelium preserving methodology. Furthermore, our procedure is 5 times more efficient than the current gold standard, which requires removal of the epithelium.

Figure 2:
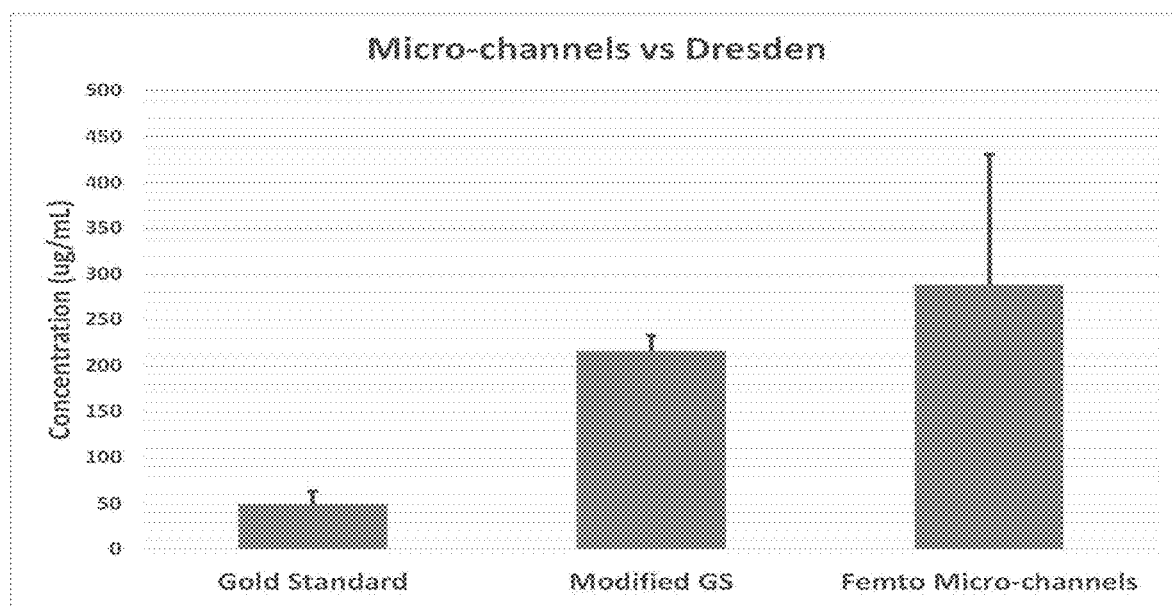
FIG. 2. Comparison of delivery efficiencies for various methods, including the previous epithelium off Gold Standard (GS—Dresden Protocol), an epithelium off Modified GS using 0.5% Riboflavin and our epithelium on method (Femto Micro-channel).

We have developed a working device suitable for ex-vivo and in-vivo animal experiments. FIG. 2 shows stromal riboflavin concentration data in the ex-vivo rabbit eye comparing our procedure (settings: 25 um channel spacing, 10 uJ pulse energy, 6 mm diameter treatment area, 1030 nm wavelength) to the Dresden protocol (0.1% riboflavin, epi-off) and a modified Dresden protocol (0.5% riboflavin, epi-off).

Photo-disruption is a process that "vaporizes" or removes material within the focal volume of a high intensity femtosecond laser. Our procedure creates well defined channels in the cornea epithelium with an amplified femtosecond laser (or any laser for that matter) for the purpose of enhanced transepithelial fluorophore/drug delivery.

Currently, there are two methods used for transepithelial corneal drug delivery. First, numerous chemical agents are used to loosen the tight junctions of the superficial epithelium, thus increasing the permeability of the cornea to the aqueous drug solution of interest. Second, to promote iontophoresis, a somewhat cumbersome device is placed on the corneal surface for the purpose of generating a voltage potential across the cornea towards the interior of the eye. This ultimately drives the drug into the cornea along the electric potential gradient. Our device is clearly different from these two methods.

However, our device is somewhat similar to other devices. Specifically, medical ophthalmic lasers, such as the Intralase and LensX, also employ amplified femtosecond lasers at or near 1030 nm to photo-disrupt ocular tissues. The Intralase uses amplified femtosecond pulses and a galvo-mirror scanning delivery system to photo-disrupt millions of overlapping micron sized spots in the cornea, thus creating a continuous resected plane within the cornea. The LensX device fulfills a similar purpose in the lens capsule for cataract surgery. The purpose of both devices is to cut ocular tissue, thus replacing mechanical blades that were used prior. Our device is composed of elements similar to these two devices. All three devices possess the following: 1) anamplified femtosecond laser engine; 2) X-Y axis scanning galvo mirrors and control software/system to control the position of the laser focal spot within the tissue; 3) objective lens/delivery optics to focus the laser into the sample; and 4) a contact interface between laser delivery and cornea. All three devices use femtosecond laser photo-disruption as the driving principle for their respective technologies.

We use a laser (e.g., a commercial femtosecond laser made by OneFive) and a delivery system (e.g., commercially available x-y-z galvo scanning mirrors+focusing objective) in our device. Our procedure uses an amplified femtosecond laser and low numerical aperture femtosecond laser delivery system to create precise micron scale channels in the superficial corneal epithelium for fluorophore/drug delivery.

The laser wavelength, pulse energy, and repetition rate along with the low numerical aperture of the delivery system (NA=0.05 to 0.5) were chosen specifically, and are unique to our device/procedure, to allow for the creation of a single well defined channel (1-10 microns in diameter and 5-100 microns in length) per laser pulse in a precisely controlled pattern on the epithelial surface. These design elements are unique to our device.

The control software, which we developed, controls the galvo mirrors such that the beam is scanned in a raster pattern.

Figure 3:
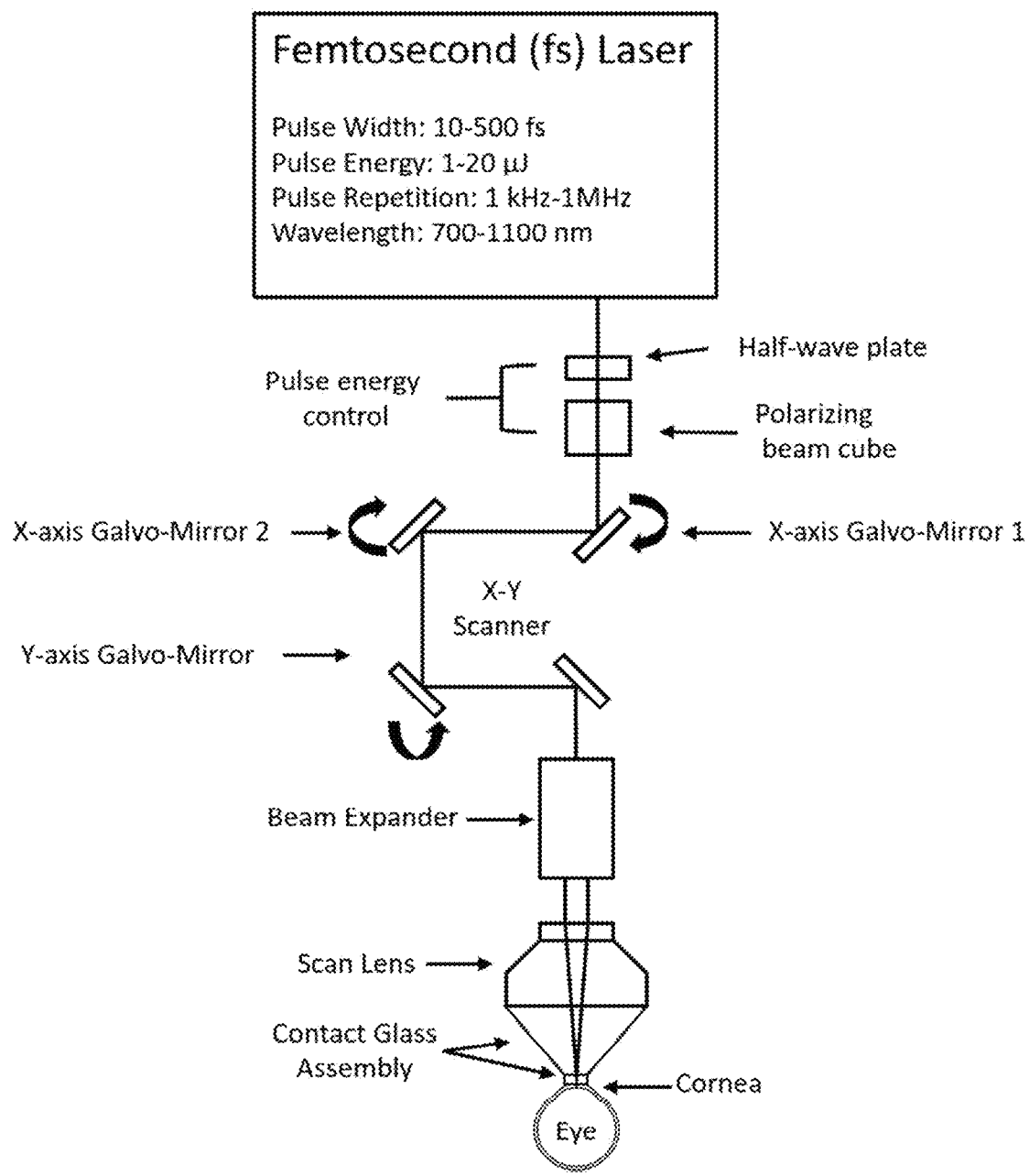
FIG. 3. A regeneratively amplified femtosecond laser micromachining device.

Referring to FIG. 3, a regeneratively amplified femtosecond laser (commercially available) with the following characteristics is used in this device: 1. Pulse duration is 10-500 fs. 2. The pulse energy is 1-20 µJ. 3. The pulse repetition rate is 1 kHz-1 MHz. 4. The wavelength is 700-1100 nm. The laser first passes through a half-wave plate and a polarizing beam cube, which together modulate pulse energy. The beam then passes through 3 galvo controlled mirrors (2 galvos for X-axis, 1 galvo for y-axis) which through their programmed rotation can scan the beam in any arbitrary pattern in the work piece, in this case a raster pattern on or within the corneal epithelium. After the x-y scan mirrors the beam passes through a beam expander (commercially available) to condition/optimize the beam for the scan lens/objective. Next the beam passes through a scanning lens with a numerical aperture, NA, between 0.05 to 0.5 (commercially available). This lens focuses the laser into the corneal epithelium. After the scanning lens, there is a contact glass assembly which comes into contact with the corneal epithelium. This ensures that the laser is focused at the correct depth within the epithelium during the scan.

Figure 4:
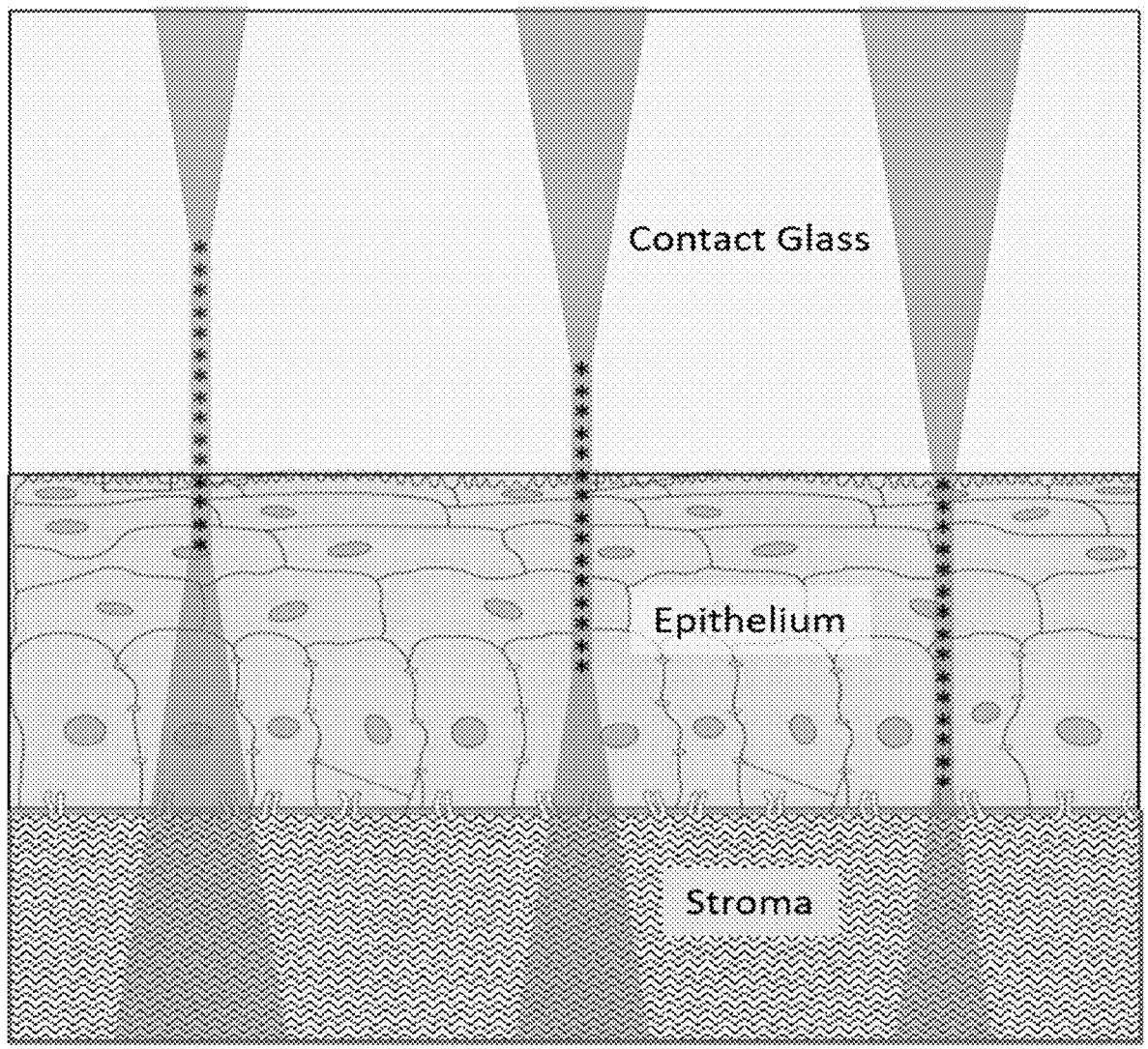
FIG. 4. Interface of a contact glass assembly and a corneal epithelium. The asterisks indicate where photo-disruption occurs.

Referring to FIG. 4, the interface of the contact glass assembly and the corneal epithelium is shown. The figure also shows representative focal depths attainable in the corneal epithelium. Channels are created along the focal volume of the scan lens, which are elongated and narrow due to the low numerical aperture chosen for our application. The focal plane of the laser is controlled and can be set to not extend past the epithelium or into the stroma. The asterisks indication where photo-disruption occurs. Outside of this region the tissue in unperturbed. As shown, these channels extend through superficial corneal epithelium toward the underlying corneal stroma and are oriented substantially parallel to the optical axis of the cornea.

Figure 5:
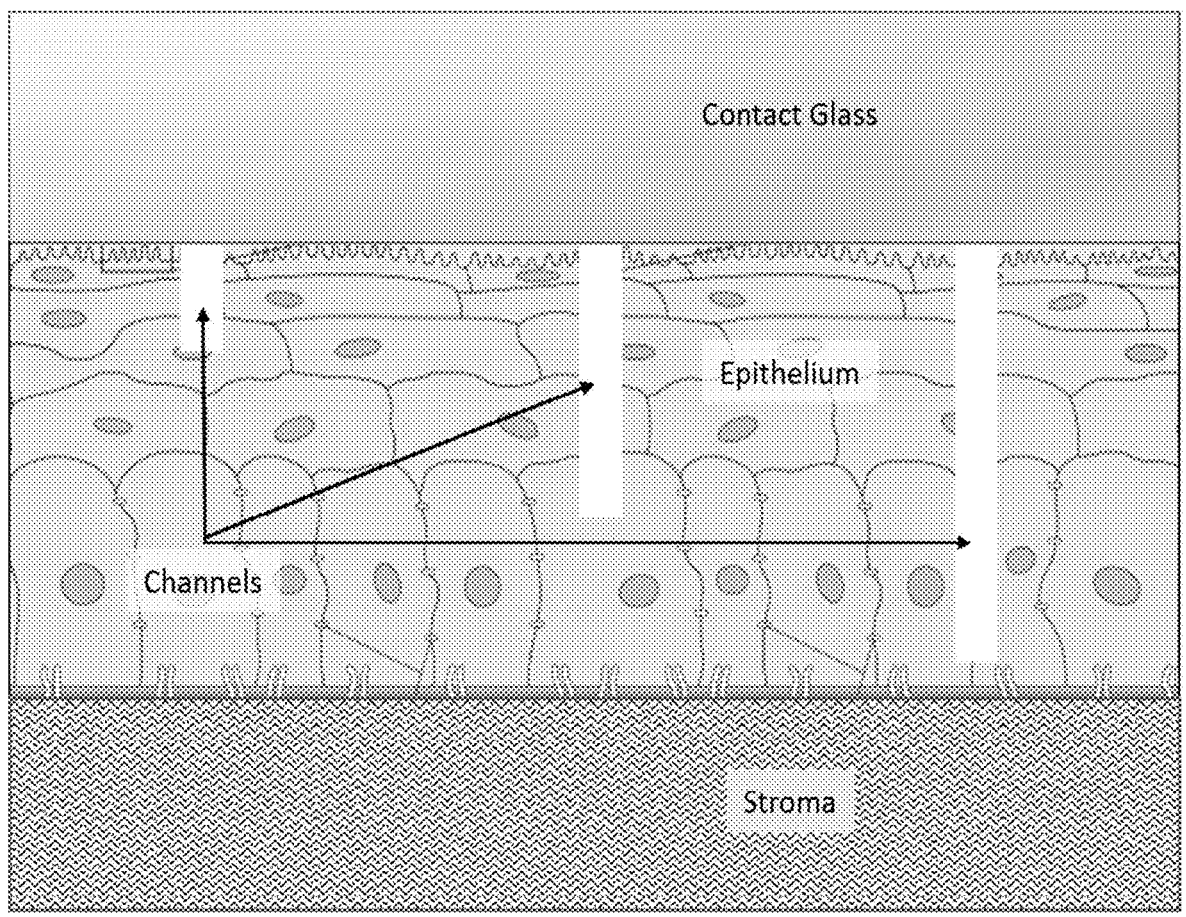
FIG. 5. Illustration of what created channels would look like for the indicated laser focal depths in FIG. 4.

Referring to FIG. 5, the figure illustrates what the channels would look like for the laser focal depths from the previous figure. The channels do not extend into the stroma. The spacing and depth are entered into the control software.

Figure 6:
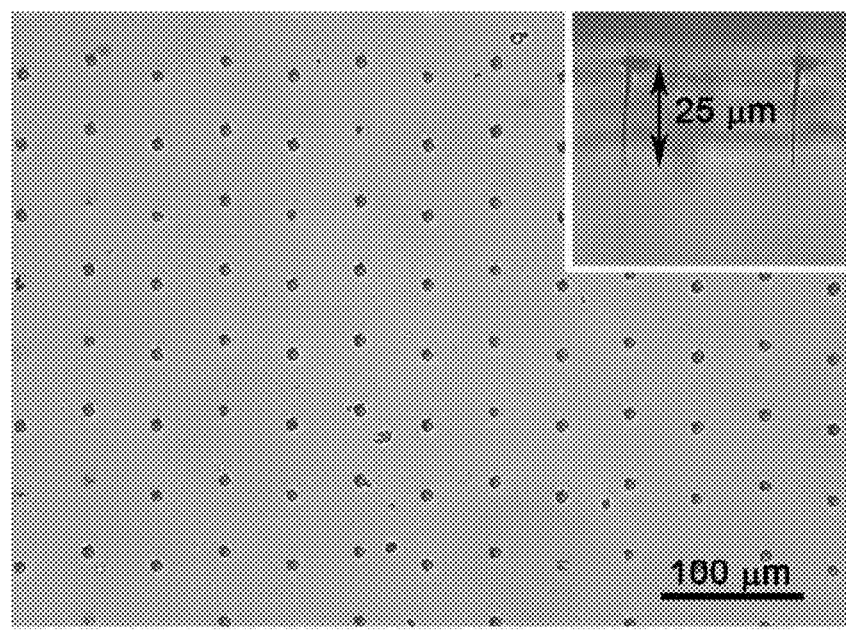
FIG. 6. Microchannels created in a silicon sheet viewed on the surface showing 100 µm spot separation. Insert shows silicon sheet cut in cross section along the microchannels and illustrates the depth of the microchannels that measure 25 µm.

Referring to FIG. 6, a raster pattern of surface channels created in silicon is shown. The spacing in this figure is 100 µm but can be varied arbitrarily in the software which controls the x-y galvo mirrors. The diameter of these channels is roughly 5 µm. They extend roughly 25 µm deep into the silicon as shown in the figure insert. This is the same pattern that is generated in the corneal epithelium. The riboflavin or drug of interest in solution flows through these channels and into the stroma, thus bypassing the impermeable epithelium. The area disrupted in the epithelium is relatively small. As such the epithelium heals and closes up these channels within hours.

Figure 7:
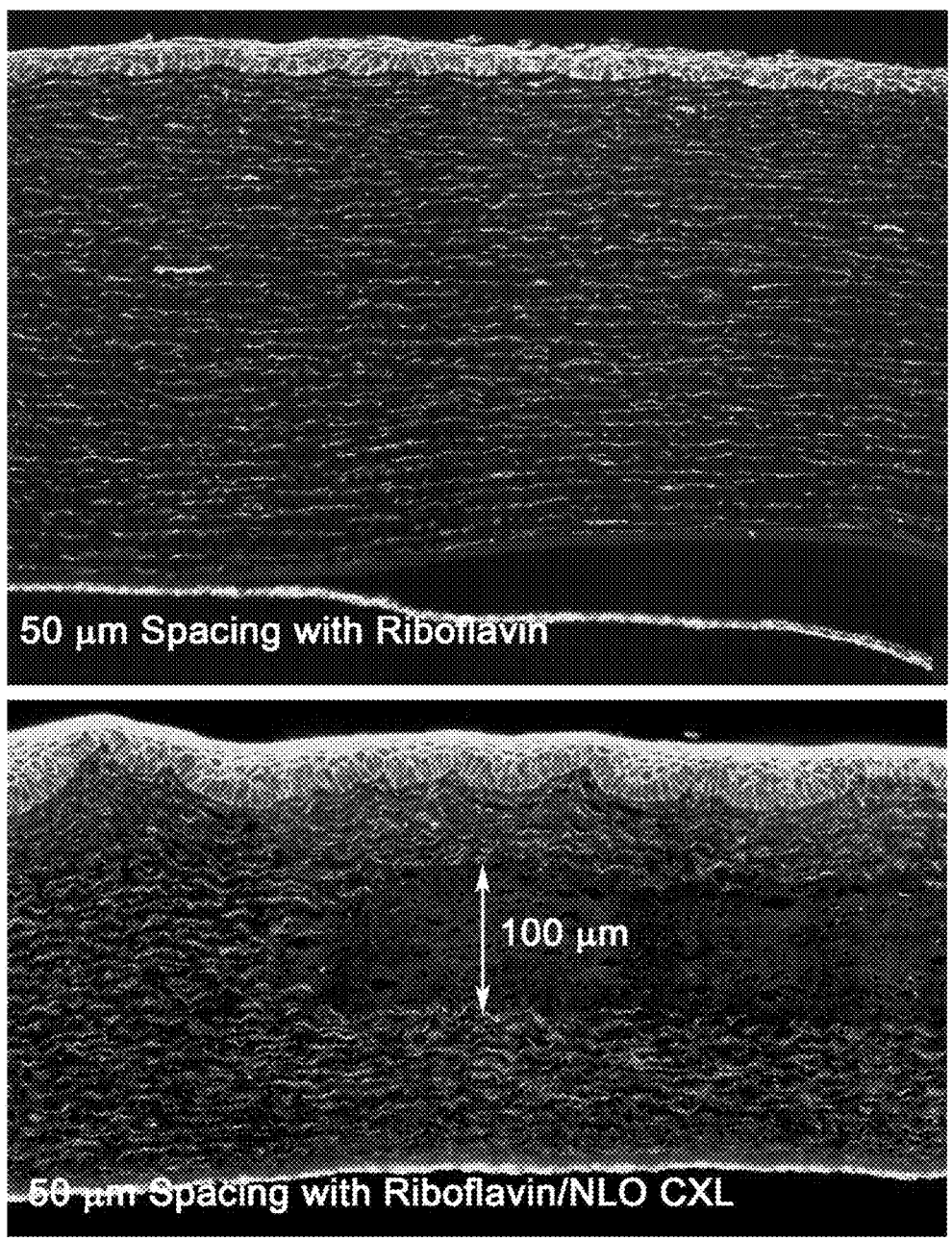
FIG. 7. Corneal images: (above) before and (below) 24 hours after non-linear optical cross-linking. The epithelium is intact and fully healed 24 hours after channel creation and the channels are not detectable.

Surprisingly and unexpectedly, the channels created by our device and procedure permit unparalleled delivery of therapeutic agents, e.g., riboflavin, into the corneal stroma. Also surprisingly, it is not possible to detect the channels following a healing period following creation of the channels. For example, referring to FIG. 7, channels formed during non-linear crosslinking are fully healed within 24 hours after channel creation. It is not possible to detect that the channels were even there.

Some embodiments relate to induction of wound healing in a cornea. For example, such wound healing may be used to tack a corneal epithelium down to a cornea. This is necessary in some epithelial dystrophies where a corneal epithelium is detached from a cornea. Previously, such conditions have been treated with either corneal transplantation or micropuncture using bent needles.

It is to be appreciated that, although the above disclosure refers to certain examples or embodiments, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for creating a plurality of micro-channels which extend through superficial corneal epithelium toward underlying corneal stroma and are oriented substantially parallel to the optical axis of the cornea, wherein the system comprises:
    (a) a femtosecond laser having a pulse energy range of 1 to 20 microjoules (uJ) and a capability of generating a laser beam having a wavelength of 700-1100 nanometers (nm) and a repetition rate of 1 kilohertz to 1 megahertz,
    (b) a laser delivery system comprising a beam expander, a scanning lens having a numerical aperture (NA) of 0.05 to 0.5 and a focusing objective, and
    (c) control software that controls the spacing, depth and pattern of said micro-channels created by laser energy emitted from the femtosecond laser;
    wherein the femtosecond laser and laser delivery system are useable to create said micro-channels which extend through superficial corneal epithelium toward underlying corneal stroma and substantially parallel to the optical axis, and
    wherein the control software enables a user to control the femtosecond laser so that the lengths and diameters of said microchannels will be suitable to accomplish at least one purpose selected from: facilitating crosslinking corneal collagen, increasing delivery of a drug or therapeutic substance, treating of infection, tacking down of the corneal epithelium to the cornea, killing cells, bacteria, tumors or neovascular vessels growing into the cornea, inducing wound healing in the cornea and treating epithelial dystrophy.

2. The system according to claim 1, wherein the femtosecond laser is a regeneratively amplified femtosecond laser having a pulse duration of 10-500 fs.

3. The system according to claim 1, wherein the laser delivery system comprises galvo controlled mirrors for control of the laser beam in x, y and z dimensions.

4. The system according to claim 3, wherein there are one or more galvo mirrors for control of the laser beam in the x-axis, and one or more galvo mirrors for control of the laser beam in the y-axis.

5. The system according to claim 4, wherein there are two galvo mirrors for control of the laser beam in the x-axis, and one galvo mirror for control of the laser beam in the y-axis.

6. The system according to claim 1, wherein the scanning lens has a numerical aperture of 0.1-0.3.

7. The system of claim 1, wherein the control software is configured to control delivery of the laser beam in a raster pattern.

8. A method of inducing wound healing in a cornea in a subject comprising:
   (a) providing a system according to claim 1; and
   (b) using the system to direct the femtosecond laser through the cornea epithelium and into the stroma of the cornea to create said plurality of said micro-channels such that they extend through the corneal epithelium and into the cornea and are substantially parallel to the optical axis of the cornea, and
   wherein the control software is used to select the diameters and lengths of said micro-channels so that the micro-channels induce wound healing in the cornea.

9. A method of noninvasively increasing corneal epithelial permeability to a therapeutic agent, the method comprising:
   (a) providing a system for creating micro-channels through superficial corneal epithelium, the system comprising: i) a femtosecond laser having a pulse energy range of 1 to 20 microjoules (uJ) and a capability of generating a laser beam having a wavelength of 700-1100 nanometers (nm) and a repetition rate of 1 kilohertz to 1 megahertz, ii) a laser delivery system comprising a beam expander, a scanning lens having a numerical aperture (NA) of 0.05 to 0.5 and a focusing objective, and iii) control software that controls the delivery system such that the laser beam is scanned in a pattern;
   (b) using the system to direct the femtosecond laser through the corneal epithelium to create a said plurality of micro-channels such that they extend through the corneal epithelium and no further than the basal epithelial layer, and
   (c) applying the therapeutic agent to the permeabilized corneal epithelium so that the therapeutic agent passes through the micro-channels and into the corneal stroma.

10. The method of claim 9, wherein the wherein each of said micro-channels 1-10 μm in diameter and 5-100 μm in axial length.

11. The method of claim 9, wherein the micro-channels are created in a raster pattern.

12. The method of claim 9 wherein the grid pattern has an inter-spot spacing from 25 to 250 μm.

13. The method of claim 9, wherein the therapeutic agent comprises a drug and/or a photodynamic agent.

14. The method of claim 13, wherein the drug is riboflavin 5' phosphate.

15. The method of claim 14, wherein a concentration of the riboflavin 5' phosphate delivered to the corneal stroma is about 300 μg/ml.

16. The method of claim 9, wherein the femtosecond laser is used at a 10 μJ pulse energy and a wavelength of about 1030 nm.

17. The method of claim 9, wherein a 6 mm diameter area is treated and the micron-scale channels have a 25-250 μm channel spacing.

18. The method according to claim 9, further comprising applying non-linear optical photodynamic therapy to the cornea comprising directing pulsed infrared laser light at a focal spot at a depth in the cornea, wherein the pulsed infrared laser light causes collagen crosslinking (CXL) and resultant corneal stiffening.

19. The method according to claim 9, further comprising applying non-linear optical photodynamic therapy to the cornea comprising directing pulsed infrared laser light at a focal spot at a depth in the cornea, wherein the pulsed infrared laser light within the cornea treats a corneal infection.

20. The method according to claim 9, further comprising applying non-linear optical photodynamic therapy to the cornea comprising directing pulsed infrared laser light at a focal spot at a depth in the cornea, wherein the pulsed infrared laser light kills cells, bacteria, tumors or neovascular vessels growing into the cornea.

21. A method for inducing wound healing in a cornea in a subject, said method comprising:
   (a) providing a system for creating micro-channels through superficial corneal epithelium, the system comprising: i) a femtosecond laser having a pulse energy range of 1 to 20 microjoules (μJ) and a capability of generating a laser beam having a wavelength of 700-1100 nanometers (nm) and a repetition rate of 1 kilohertz to 1 megahertz, ii) a laser delivery system comprising a beam expander, a scanning lens having a numerical aperture (NA) of 0.05 to 0.5 and a focusing objective, and iii) control software that controls the delivery system such that the laser beam is scanned in a pattern;
   (b) using the system to direct the femtosecond laser through the cornea epithelium and into the stroma of the cornea to create micron-scale channels through the corneal epithelium and into the cornea,
   wherein the micro-channels induce wound healing in the cornea; and
   wherein the wound healing is accompanied by tacking down of the corneal epithelium to the cornea.

22. The method of claim 21, wherein the method is carried out to treat epithelial dystrophy.

* * * * *